United States Patent [19]

Mody

[11] 4,323,537
[45] Apr. 6, 1982

[54] ANALYSIS SYSTEM

[75] Inventor: Dinesh I. Mody, Bedford, Mass.

[73] Assignee: Instrumentation Laboratory Inc., Lexington, Mass.

[21] Appl. No.: 198,632

[22] Filed: Oct. 20, 1980

[51] Int. Cl.³ .................. G01N 1/14; G01N 35/00
[52] U.S. Cl. ............................. 422/63; 141/130; 422/65; 422/81; 422/100
[58] Field of Search ............... 422/63, 81, 64, 65, 422/100; 141/130; 73/425.4 R, 425.6; 134/22 R, 37

[56] References Cited

U.S. PATENT DOCUMENTS

| | | | |
|---|---|---|---|
| 3,241,923 | 3/1966 | Ferrari | 23/259 |
| 3,609,040 | 9/1971 | Kuzel | 356/36 |
| 3,687,632 | 8/1972 | Natelson | 422/65 |
| 3,826,621 | 7/1974 | Johnson, Jr. et al. | 422/100 |
| 3,842,680 | 10/1974 | Vollick | 73/425.4 |
| 3,858,450 | 1/1975 | Jones | 422/100 X |
| 3,858,450 | 1/1975 | Jones | 73/423 A |
| 3,900,289 | 8/1975 | Liston | 23/230 R |
| 3,912,456 | 10/1975 | Young | 23/253 R |
| 4,000,973 | 1/1977 | Petersen | 23/230 R |
| 4,054,415 | 10/1977 | Seligson | 23/253 R |
| 4,076,503 | 2/1978 | Atwood | 23/259 |
| 4,108,602 | 8/1978 | Hanson | 23/230 R |
| 4,217,780 | 8/1980 | O'Connell | 73/421 R |
| 4,245,509 | 1/1981 | Mody | |
| 4,252,769 | 2/1981 | Hood et al. | 422/81 X |

OTHER PUBLICATIONS

Finley, Paul R., et al., "Evaluation of a New Multichannel Analyzer, 'Astra-8'", Clin. Chem., vol. 24, No. 12 (1978), pp. 2125-2131.

Primary Examiner—Ronald Serwin

[57] ABSTRACT

A liquid handling system that is particularly useful in a clinical analysis system and includes first and second storage chambers, each with a port through which liquid may be flowed into and from the storage chamber. The storage chambers and their ports are arranged to permit concurrent flowing of liquids from both storage chambers into a processing chamber. The system also includes two liquid metering means and a diluent reservoir. A valve arrangement enables connection of one of the metering means to the diluent reservoir and to either of the storage chambers; and each metering means, when connected to a storage chamber, controls flow of liquid into and out of the storage chamber through its port. The two metering means and the valve arrangement provide flexibility in selecting dilution ratios and delivering raw and diluted sample as required to an array of chambers for analysis or other processing.

21 Claims, 11 Drawing Figures

ANALYSIS SYSTEM

This invention relates to analysis systems and more particularly to liquid handling apparatus for delivering mixtures of liquids in predetermined proportions to analysis chambers for measurement or other testing.

In an automated clinical analysis system, the sample fluid to be analyzed is frequently diluted to provide a sample volume which can be more easily processed. In the case of a chemical analysis, raw or dilute sample may be mixed with a reactant for analysis. For example, in a clinical chemistry analysis system, minute quantities of a serum sample are mixed with various quantities of different reagents to provide chemical reactions that enable measurement of particular constituents of the serum sample.

A number of different liquid handling arrangements have been proposed for use in analysis systems of these types, none of which is fully satisfactory. In general, a multi-channel clinical chemistry analysis system should have capability of providing a wide range of dilution ratios. Accurate measurement and thorough mixing are essential. Preferably, required volumes of sample and reagents must be provided in precise proportion for accurate analysis; and sample preparation time should be minimized. In addition storage and analysis chambers must be thoroughly cleaned to avoid cross-contamination between successive samples.

In accordance with one aspect of the invention, there is provided a liquid handling system that is particularly useful in a clinical analysis system and includes first and second storage chambers, each with a port through which liquid may be flowed into and from the storage chamber. The storage chambers and their ports are arranged to permit concurrent flowing of liquids from both storage chambers into a processing chamber. The system also includes two liquid metering means and a diluent reservoir. A valve arrangement enables connection of one of the metering means to the diluent reservoir and to either of the storage chambers; and each metering means, when connected to a storage chamber, controls flow of liquid into and out of the storage chamber through its port. The two metering means and the valve arrangement provide flexibility in selecting dilution ratios and delivering raw and diluted sample as required to an array of chambers for analysis or other processing.

In preferred embodiments, each storage chamber is in the form of an elongated flexible tube and each chamber port is formed in a probe member that is connected to the tube and is mounted for movement into and out of a processing chamber. The two probes are mounted on a transport carriage for movement as a unit between a sampling station where a sample of fluid to be analyzed is drawn into a storage chamber through its associated probe port and a series of processing stations where predetermined quantities and ratios of sample fluid and diluent, or diluted sample fluid are metered into processing chambers.

Also, in preferred embodiments each metering means includes a positive displacement pump, one metering pump preferably having a larger capacity then the other metering pump, which differential capacity in a particular embodiment is provided by use of pump cylinders of different diameter, the lower capacity pump having greater metering precision.

In accordance with another feature, structure mounted on a probe transport carriage defines a chamber that houses the probe tip and has a port. Means are provided to flow air into the chamber through the port and along the outer surface of the probe for withdrawing excess liquid from the probe tip and flowing that withdrawn liquid over the outer surface of the probe to waste. This feature enables cleaning and geometry adjustment of the liquid at the tip of the probe for precision metering, as well as providing a probe cleaning capability. In a particular embodiment, the probe is a stainless steel tube with an outer diameter of about $1\frac{1}{2}$ millimeters and the chamber is an open ended cylindrical bore which houses the probe tube with clearance of about 0.05 millimeter. Vacuum (a pressure differential of about fifteen inches of mercury), is applied to the bore over about one centimeter probe length and draws liquid flowing from the probe at a rate of 125 microliters per second upwardly over the outer surface of the probe without discharge of any liquid from the open, lower end of the bore. The feature permits dispensing of relatively large volumes of liquid for cleaning the outer surface of the probe, as well as dispensing of small volumes for clearing a potential contaminent (such as a reagent from the previous analysis station), to provide a fresh liquid surface, or to adjust the liquid surface immediately prior to dispensing of liquid to avoid possible errors due to evaporation. Where desired, the liquid surface may be drawn away from the probe tip to provide an isolation air bubble between different liquids.

In a particular embodiment, an analysis system includes a sample station with a sample transport mechanism for positioning a sample container at the sample station, a plurality of analysis stations, each having an analysis cuvette, and a supplementary station with a mixing chamber. The system includes two transport carriages, one serving a chemistry analysis section and the other serving an electrolyte analysis section. Each carriage supports two liquid handling probes and is sequenced between the sample, supplemental, and analysis stations by a digitally controlled stepper motor drive. Mounted on each carriage is structure that defines two parallel cylindrical passages in which the tips of the stainless steel probe tubes are housed. A vacuum system connected to each passage is arranged to maintain a continuous flow of air upwardly through the bore along the lower outer surface of the probe. Each probe is movable between a retracted position in which the probe tip is housed in the bore and a transfer position in which the probe tip is inserted into a chamber at a sample, analysis, or supplemental station for injecting or withdrawing liquid through the probe.

Connected to each probe is an elongated tubular flexible storage chamber and each storage chamber is connected to a main metering pump via a valve arrangement. The valve arrangement includes a first three-way valve arranged to alternately connect the two storage chambers to a second three-way valve, the common port of which is connected to the main metering pump with its third port connected to the diluent reservoir. The arrangement allows the main metering pump to control priming of the system and both storage chambers with diluent, the aspiration of liquid into either storage chamber and the dispensing of liquid from either storage chamber. A second metering pump of greater precision than the main metering pump controls the aspiration and dispensing of small quantities of liquid from one of the storage chambers through its probe.

Each metering pump is a positive displacement device that includes a precision bore cylinder with a reciprocable piston that is driven by a stepping motor through a precision lead screw, the cylinder of the pump of greater precision having a smaller diameter bore than the cylinder of the main pump.

An analysis station includes a reaction chamber cup mounted for bidirectional rotation and a dedicated reagent dispenser. A supplemental processing chamber, also in the form of a cup mounted for bidirectional rotation, and into which the two probes may be concurrently inserted, provides predilution capability.

In a typical sequence the system line and probes are initially filled with diluent from the diluent reservoir by the main metering pump, and the transport carriage is positioned over the sample container at the sample station. A probe is inserted into the sample cup and the main metering pump withdraws a predetermined amount of sample and stores it in the storage tube. The probe is then raised and the carriage moved to the dilution station where both probes are inserted into the cup and the precision metering pum dispenses a predetermined amount of sample from its storage tube and the main metering pump concurrently dispenses a predetermined amount of diluent from the other storage tube. After mixing, the main metering device draws a predetermined amount of diluted sample into a storage tube (with an isolation air bubble between the diluent and the diluted sample). The carriage is then sequentially positioned at a series of analysis station. At each station, after a fresh interface of diluted sample is provided at the probe tip by dispensing a small amount of liquid from the probe while it is housed in the vacuum bore, the probe is lowered into the analysis container for dispensing a predetermined amount of diluted sample where it is mixed with a predetermined amount of reagent from the dedicated metering pump for analysis.

The particular embodiment is a clinical analysis system for analyzing biological fluids such as plasma/serum, urine and spinal fluids and includes two analysis sections, each of which is serviced by a dual probe assembly mounted on a transport carriage for movement between a sampling station for aspirating a sample to be analyzed and a series of processing stations where the sample is diluted and/or mixed with reagent for performing several different analysis utilizing a single sample of less than one-quarter milliliter volume in a cycle time of about one-half minute.

BRIEF DESCRIPTION OF THE DRAWINGS

Other features and advantages of the invention will be seen as the following description of a particular embodiment progresses, in conjunction with the drawings, in which.

DESCRIPTION OF PARTICULAR EMBODIMENT

Figure 1:
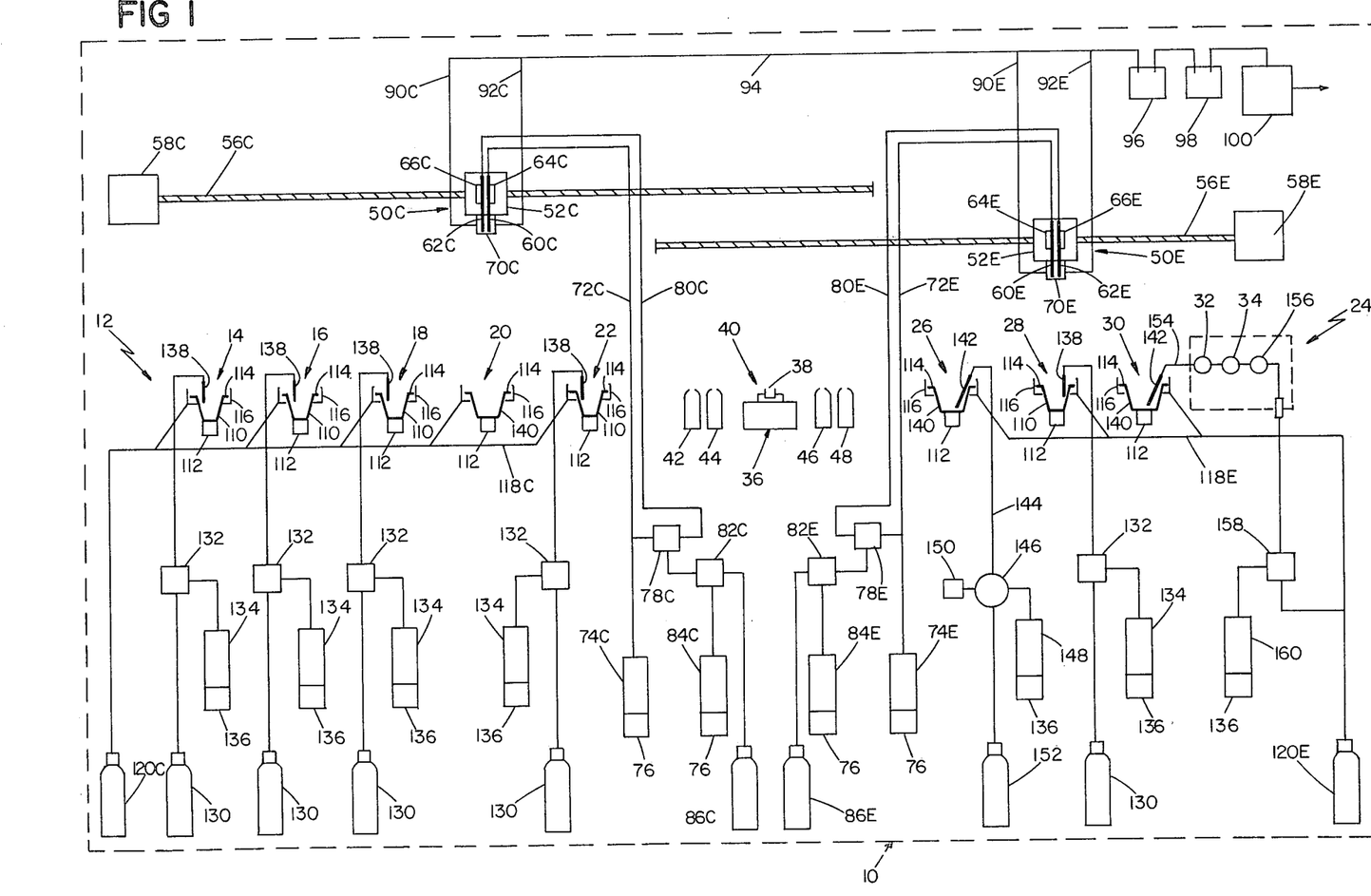
FIG. 1 is a diagrammatic view of an analysis system in accordance with the invention.

Shown in the diagrammatic view of FIG. 1 is a clinical analysis system that includes support frame structure 10 on which is mounted a chemistry analysis section 12 that includes a total protein analysis station 14, a glucose analysis station 16, a BUN analysis station 18, a utility station 20, and a creatinine analysis station 22; and an electrolyte analysis section 24 that includes a total carbon dioxide analysis station 26, a chloride analysis station 28, and a Na-K analysis station 30 that includes a potassium sensing electrode assembly 32 and a sodium sensing electrode assembly 34.

Located between chemistry analysis section 12 and electrolyte analysis section 24 is a sample container transport system 36 for sequentially positioning sample containers 38 (of 250 microliters size) at sample station 40. Mounted on either side of transport 36 are calibrant reservoirs 42, 44 (for the chemistry analysis section) and 46, 48 (for the electrolyte analysis section).

Associated with each analysis section is a dedicated dual probe assembly 50 that includes a transport carriage 52 supported on a drive and guide assembly that includes a guide rail 54 and a drive screw 56 that is driven by a programmable drive motor 58. Mounted on each transport carriage 52 are two probes 60, 62, each of which has a corresponding drive mechanism 64, 66 for moving the tip 68 of its probe between a raised position in which the probe tip 68 is housed within vacuum block assembly 70 and a lower position.

Probe 60 is connected via storage chamber tube 72 to a positive displacement metering pump 74 controlled by a programmable stepping motor 76, and which has an associated three-way valve 78; and probe 62 is connected via storage tube 80 to valve 78. Connected to valve 78 via a second three-way valve 82 is a second positive displacement metering pump 84 controlled by programmable stepping motor 76. A second port of valve 82 is connected to diluent reservoir 86.

Vacuum block 70 has connections over lines 90 and 92 to common line 94 which is connected through waste bottle 96 and accummulator 98 to vacuum pump 100.

Analysis stations 14, 16, 18, 22 and 28 each includes a transparent analysis cuvette 110 that is mounted for bidirectional rotation about a vertical axis as driven by motor 112. Each cup 110 has a lip 114 that extends into an annular waste cup 116 that is connected via manifold 118 to waste container 120. Also associated with each analysis station 14, 16, 18, 22 and 28 is a dedicated reagent reservoir 130, a control valve 132 and a positive displacement metering pump 134 (with drive motor 136) for flowing reagent into its analysis cuvette 110 through reagent probe 138.

Mixing cuvettes 140 are provided at utility station 20 in the chemistry section 12 and at stations 26 and 30 in the electrolyte section 24. Each utility cup is mounted for bidirectional rotation about a vertical axis by a similar driven motor 112. Extending into cup 140 at stage 26 is an aspiration probe 142 which is connected via line 144 and valve 146 to reaction chamber 148. Also connected to valve 146 is a pressure transducer 150 and a reagent reservoir 152. A similar probe 142 at Na-K analysis station 30 is connected via line 154 to potassium analysis cuvette 33, sodium analysis cuvette 34, reference electrode 156 and three-way valve 158 which is associated with positive displacement metering pump 160. Also connected to valve 158 is waste container 162.

Further details of the dual probe assembly 50C, 50E may be seen with reference to FIGS. 2–5. Each dual probe assembly 50 is mounted on a transport carriage 52 which carries a Hall effect sensor 170 which cooperates with corresponding fixed magnets 172 at stations 20 and 26 for accurately positioning the probe carriage over the cup at that station. Upstanding from carriage 52 is frame 180 on which are mounted two probe support assemblies 182, 184. Each probe support assembly includes a sheet metal member 186 that is mounted for vertical movement as guided by guide structure 188. Each probe support bracket carries a rack gear 190 which is engaged by pinion gear 192 that is driven by drive motor 194. Biasing spring 194 returns probe arm 186 to its upper position when its drive motor 194 is deenergized. A sensor 198 mounted on support frame 180 senses the position of the probe arm 186 in its upper position.

Extending forwardly from support carriage 52 is bracket member 200 which supports two guide rods 202 (one for each probe arm 186) and vacuum block 70. The upper end of each guide rod 202 is received in a guide block 204 which is fixed to probe arm 186. At the outer end of each probe arm 186 is a support member 206 which carries probe 60 (or 62 as the case may be).

Figures 5, 6, 7:
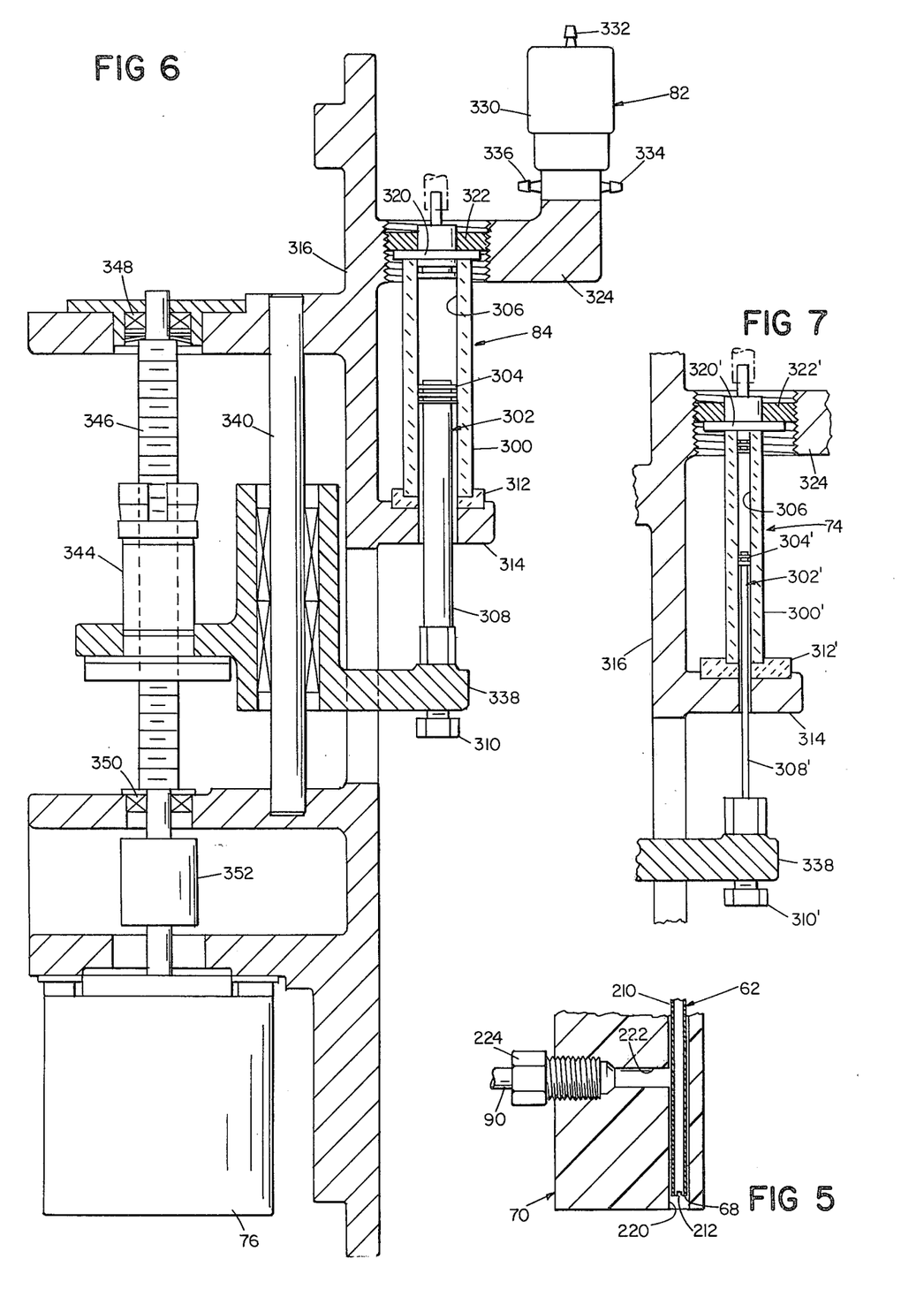
FIG. 5 is a sectional view (at an enlarged scale) showing aspects of the probe-vacuum arrangement.
FIG. 6 is a side sectional view of a programmable metering device employed in the system shown in FIG. 1.
FIG. 7 is a sectional view of a portion of a second metering device (of greater precision) employed in the system shown in FIG. 1.

Each probe 60, 62 includes a stainless steel tube 210 that has an inner diameter of about one millimeter, and outer diameter of about 1½ millimeter, and is about fifteen centimeters long. A notch 212 is formed in the lower end of each tube 210 (as indicated in FIG. 5). Secured adjacent the upper end of each tube 210 is a disc 214 which carries a spring 216, the upper end of which is seated against support 206. A tube stop 218 is seated on the upper surface of support 206.

Vacuum block 70 is of clear acrylic resin and has two parallel vertically extending through passages 220, each about 1½ millimeter in diameter, there being clearance of about 0.05 millimeter between each bore 220 and the outer surface of the probe tube 210. Intersecting each vertical passage 220 is a transverse passage 222 that is connected via connector 224 to a corresponding vacuum line 90, 92. As indicated in FIG. 5, the lower end 68 of each probe tube 210 is located about one centimeter below transverse passage 222 when the probe assembly is in its raised position. A pressure differential of about fifteen inches of mercury is continuously applied from pump 100 through accummulator 98, waste collector 96 and line 94 to lines 90 and 92 to draw liquid from the tip 68 of each probe 60, 62 upwardly over the lower portion of the probe that provides continuous cleaning capability and stabilization of the surface geometry of the liquid at the tip of each probe. The outer surface of each probe 60, 62 is cleaned additionally by flowing diluent through the probe tip 68, and drawing that diluent upwardly over the outer surface of the probe while the probe tip 68 is housed in vacuum block 70.

Figure 2:
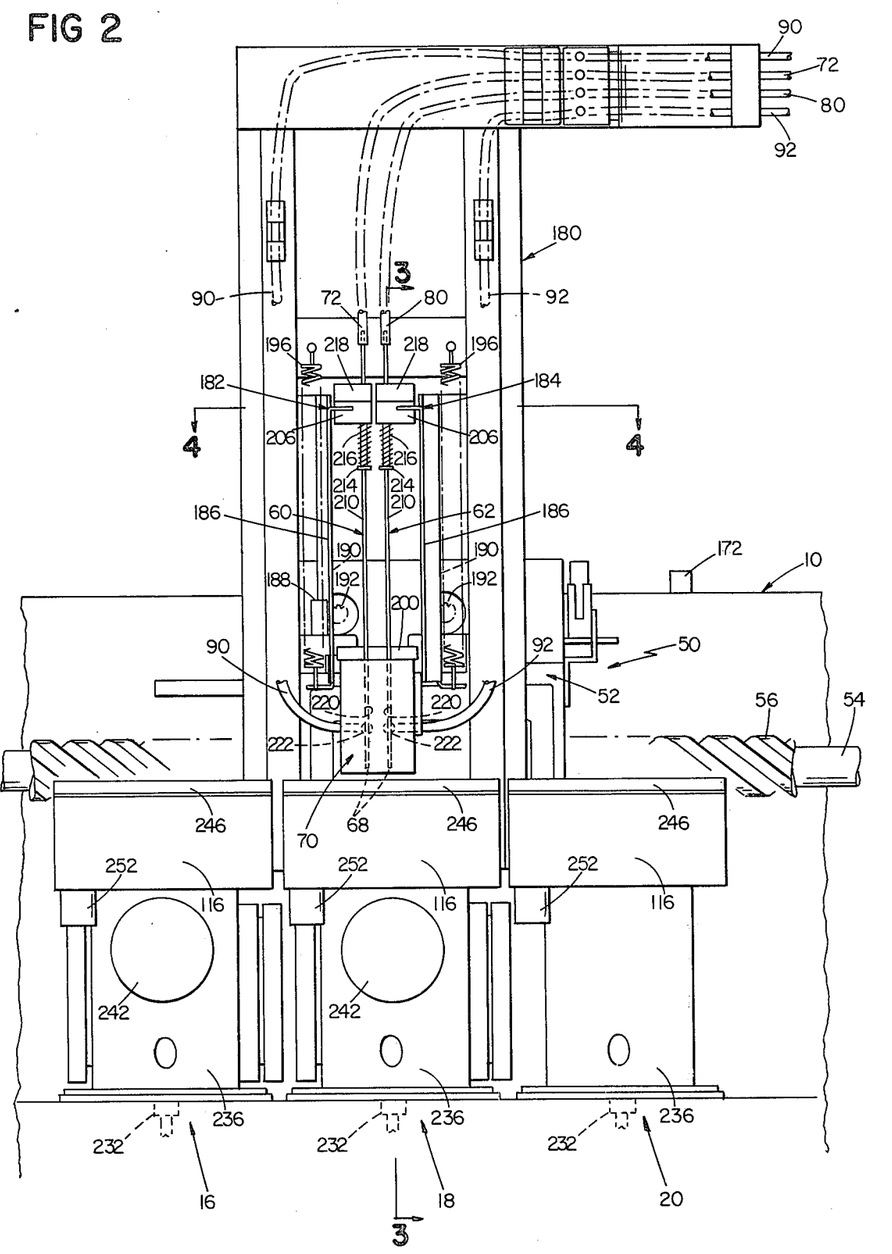
FIG. 2 is a front view of a probe transport assembly and analysis station array employed in the system shown in FIG. 1.
Figure 3:
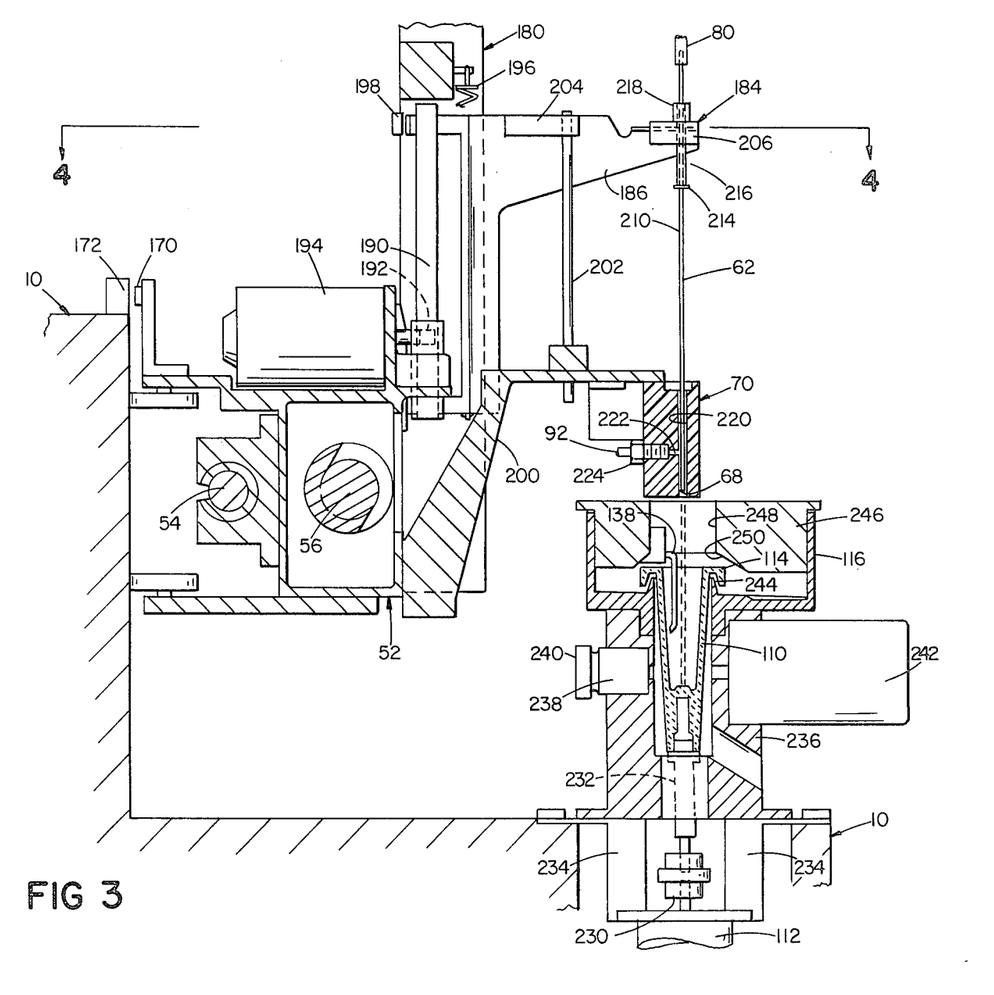
FIG. 3 is a sectional view taken along the line 3—3 of FIG. 2.
Figure 4:
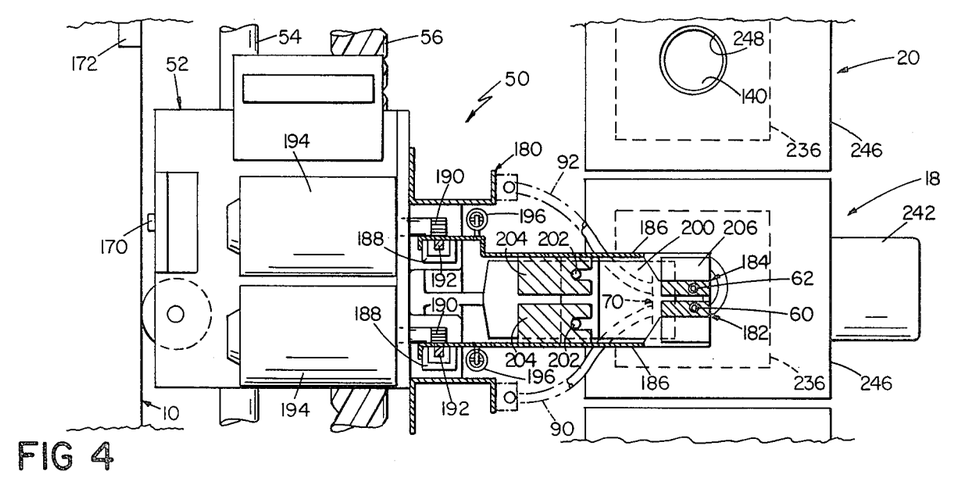
FIG. 4 is a top sectional view taken along the line 4—4 of FIG. 3.

Details of a sample analysis module may also be seen with reference to FIGS. 2–4 and particularly to the sectional view of FIG. 3. Bidirectional drive motor 112 is connected to transparent analysis cuvette 110 by coupling 230 and drive shaft 232, motor 112 being supported from system frame 10 by standoffs 234. Analysis cuvette 110 is disposed within housing 236 which supports collimator 238 for a light source 240 and a cooperating phototube sensor assembly 242. Waste cup 116 is seated on housing 236 and has an annular upwardly projecting wall 244 over which cup lip 114 extends. Waste cup 116 has a cover 246 with an aperture 248 in alignment with analysis cuvette 110 and a conical deflecting surface 250 aligned with cuvette cup lip 114. Coupling 252 (FIG. 2) at the base of each waste cup 116 provides a connection to manifold 118. Rotation of analysis cup 110 at high speed as driven by motor 112 discharges all liquid in the cup radially outward into waste cup 116 for flow through manifold 118 to waste. Reagent probe 138 is supported by waste cup 116 and extends downward into analysis cup 110 as indicated in FIG. 3. The processing cups 140 (where both probes 60, 62 enter the cup concurrently) are of a larger diameter but each is housed within a housing 236 of the same size and cooperates with a waste cup 116 of similar dimension.

Each positive displacement metering device 74, 84, 134, and 160 is of similar design, details of which may be seen with reference to FIGS. 6 and 7. Each metering device includes a cylindrical glass tube 300 in which is disposed a piston assembly 302 that includes a head portion 304 in sealing engagement with the inner surface 306 of tube 300, a shaft portion 308 and a coupling 310. The lower end of each tube is seated on a support member 312 which is received on support flange 314 of frame 316, and seated on the upper end of tube 300 is a spacer 320 secured by nut 322 on arm 324 of frame 316. Mounted on arm 324 is a three-way solenoid valve 330 that has a normally open port 332, a normally closed port 334, and a common port 336.

A controller mechanism is connected to piston 302 by means of coupling member 338 that is mounted for vertical movement along guide rod 340 as guided by ball bushing assembly 342. Carried on coupling 338 is nut 344 which cooperates with lead screw 346 that has a lead of ¼ inch. Lead screw 346 is supported in bearing assemblies 348, 350 and coupled to drive motor 76 by coupling 352. Drive motor 76 is a permanent magnetic DC stepping motor that has 200 steps for one revolution.

The metering cylinder 300 in programmable metering device 84 is a precision bore glass tube that has an inner diameter of one centimeter and a length of about 5¾ centimeters to provide an effective metering capacity of about two milliliters, and is illustrated in FIG. 6. The greater precision metering device 74 is of the same construction as metering device 84 except that its cylinder 300', as indicated in FIG. 7, is a precision bore glass tube that has an inner diameter of about 2¼ millimeters and has an effective capacity of about 0.1 milliliter.

Figure 8:
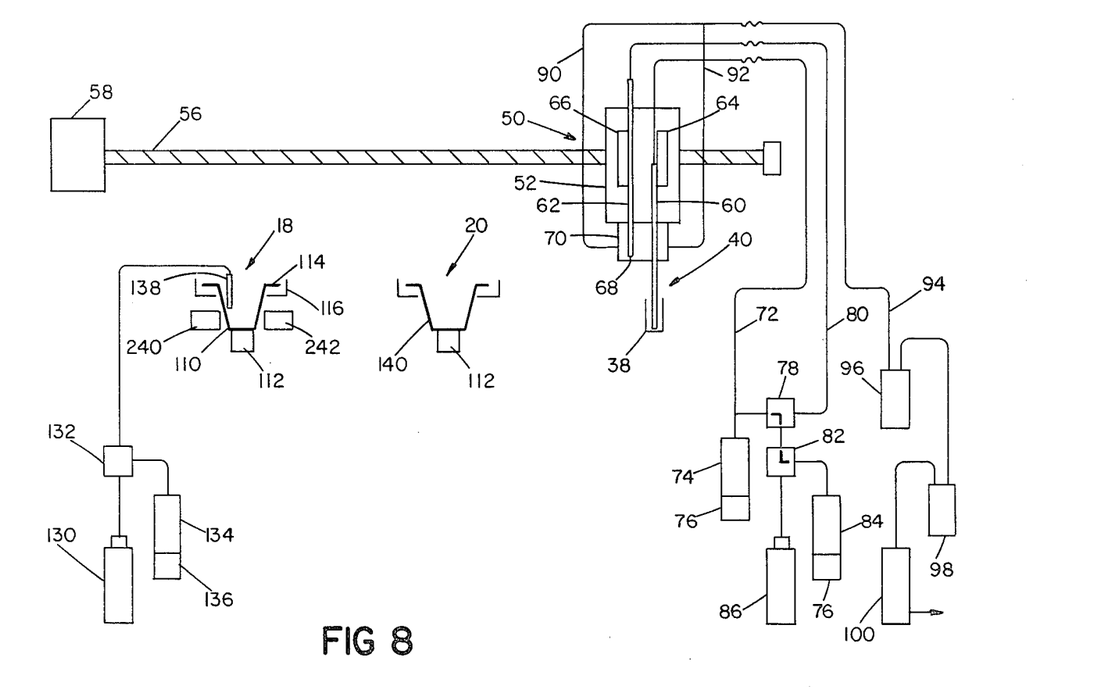
FIGS. 8-11 are a series of diagrammatic views illustrating a sequence of operations.

Further aspects of the analysis system may be seen with reference to the simplified diagrams of FIGS. 8–11 which depict a sequence of operative positions of a dual probe assembly 50. Initially, the system lines and probes 60, 62 are filled with diluent from reservoir 86. As shown in FIG. 8, assembly 50 is positioned at a sample cup station 40 with valves 78 and 82 in the indicated positions so that metering device 84 is in fluid communication with storage tube 72 and the outlet port of that storage chamber as defined by probe 60. Stepper motor 76 of metering device 84 withdraws its piston so that there is approximately fifty microliters of air volume at the tip 68 of probe 60. Probe drive 64 is energized to insert the tip of probe 60 into sample cup 38. After the tip of probe 60 is seated on the bottom of sample cup 38, the piston of metering device 84 is moved by its programmable stepping motor 76 to draw a predetermined amount of sample liquid (e.g., 100 microliters) through the probe port 68 and into the storage chamber of probe 60 and tubing 72. Probe drive 64 is then deenergized and spring 196 returns the probe 60 to its raised position (as indicated in FIGS. 2-4) with probe tip 68 positioned within vacuum block 70, and the raised probe position being indicated by interlock sensor 198.

Figure 9:
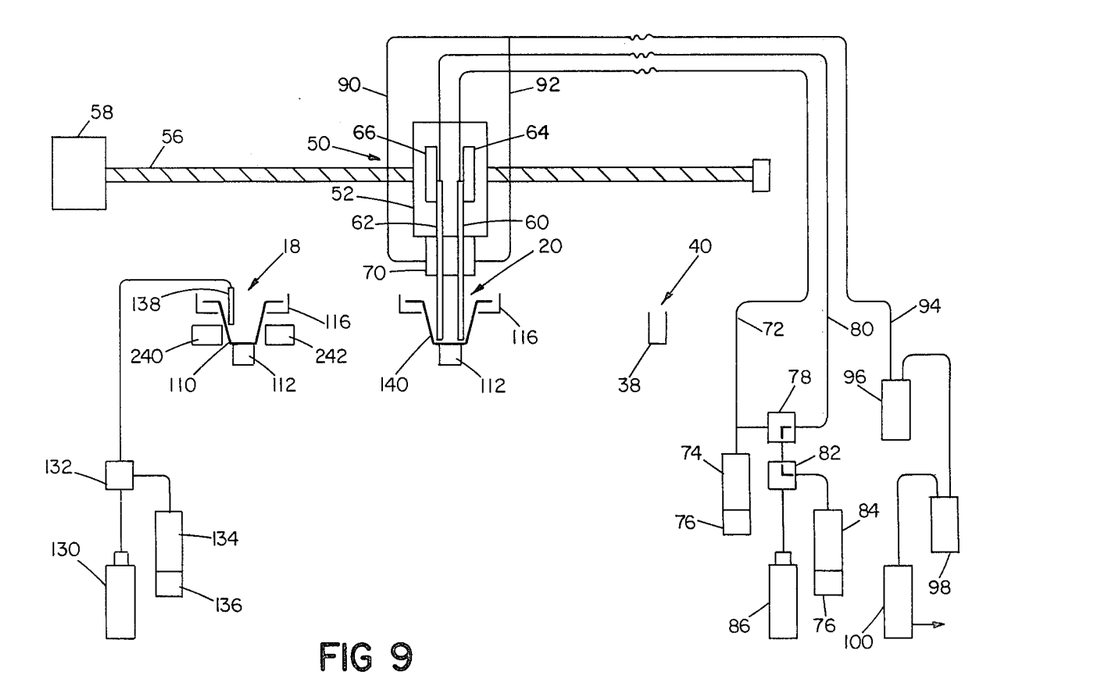

Transport motor 58 is then energized to rotate drive screw 56 to move transport carriage 52 to utility station 20 in position over utility cup 140 as indicated in FIG. 9. During that travel interval, value 78 has been shifted to connect positive displacement metering device 84 to storage line 80. Storage line 72 remains connected directly to metering device 74. When carriage 50 is directly over utility cup 140 (as verified by sensor 170), probe drives 64 and 66 are concurrently operated to lower both probes 60 and 62 into utility cup 140, and the programmable stepping motors 76 of metering devices 74 and 84 are operated to dispense a predetermined amount of sample (e.g., thirty microliters) from storage tube 72 and probe 60, and a predetermined amount of diluent (e.g., 870 microliters) from storage tube 80 and probe 62 into utility cup 140. Utility cup 140 is then subjected to a rapid sequence of bidirectional rotation (first in one direction and then in the opposite direction) to achieve thorough mixing of the sample and diluent. At this stage utility cup 140 contains 900 microliters of mixed sample and diluent at a dilution ratio of thirty.

Drive 66 then again lowers probe 62 into utility cup 140 (with a fifty microliter slug of air at the probe tip) and the piston of metering pump 84 is operated by its stepping motor 76 to withdraw a predetermined amount of diluted sample (e.g., 200 microliters) from cup 140 for storage in probe 62 and tube 80. Drive 66 is then deenergized and spring 196 returns probe 62 to its raised position with its tip 68 positioned in vacuum block 70.

Figure 10:
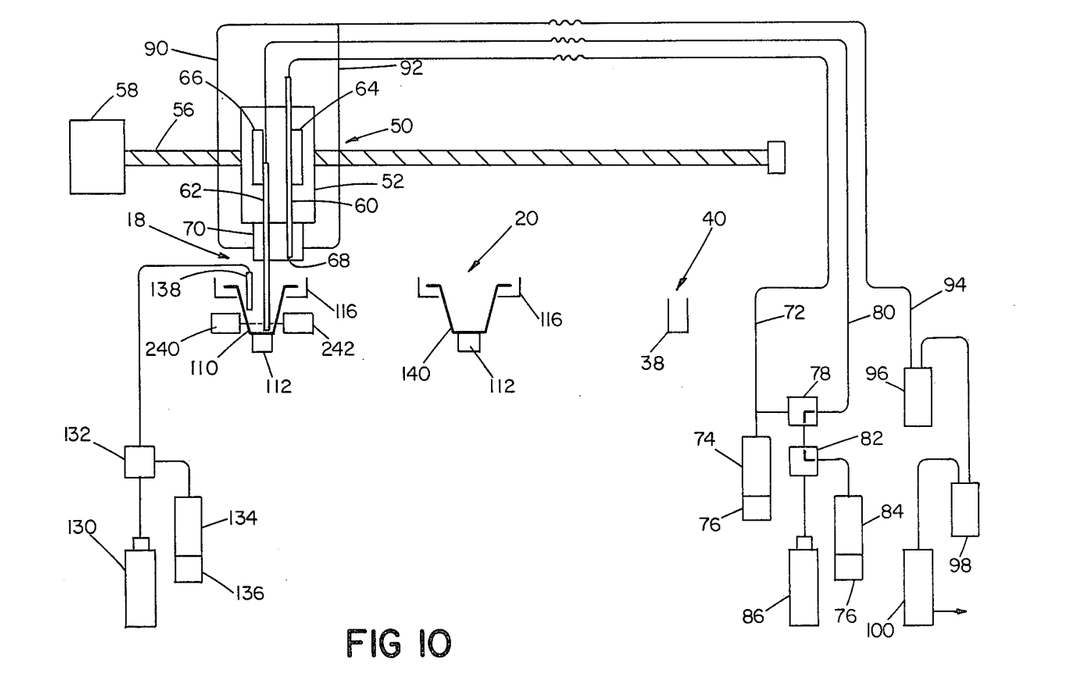

Transport motor 58 then rotates drive shaft 56 to index probe carriage 50 to position at an analysis station 18 as indicated in FIG. 10. In that carriage position, probe drive 66 is operated to lower probe 62 into analysis cup 110, and the metering piston of positive displacement metering device 84 is advanced by stepping motor 76 to dispense a predetermined amount (e.g., 75 microliters) of a diluted sample into cup 110. Concurrently, a predetermined amount (e.g., 800 microliters) of reagent is dispensed through reagent probe 138 via valve 132 and reagent metering pump 134 into analysis cuvette 110. Probe 62 is then withdrawn and the mixture of reagent and diluted sample is mixed by bidirectional rotation of analysis cuvette 110. A photometric measurement is then made by the optical system of light source 240 and sensor 242. After the analysis is completed, motor 112 drives analysis cuvette 110 at a high speed of rotation to expel the reacted dilute sample mixture from cup 110 over lip 114 into waste cup 116 for flow to waste through manifold 118.

Figure 11:
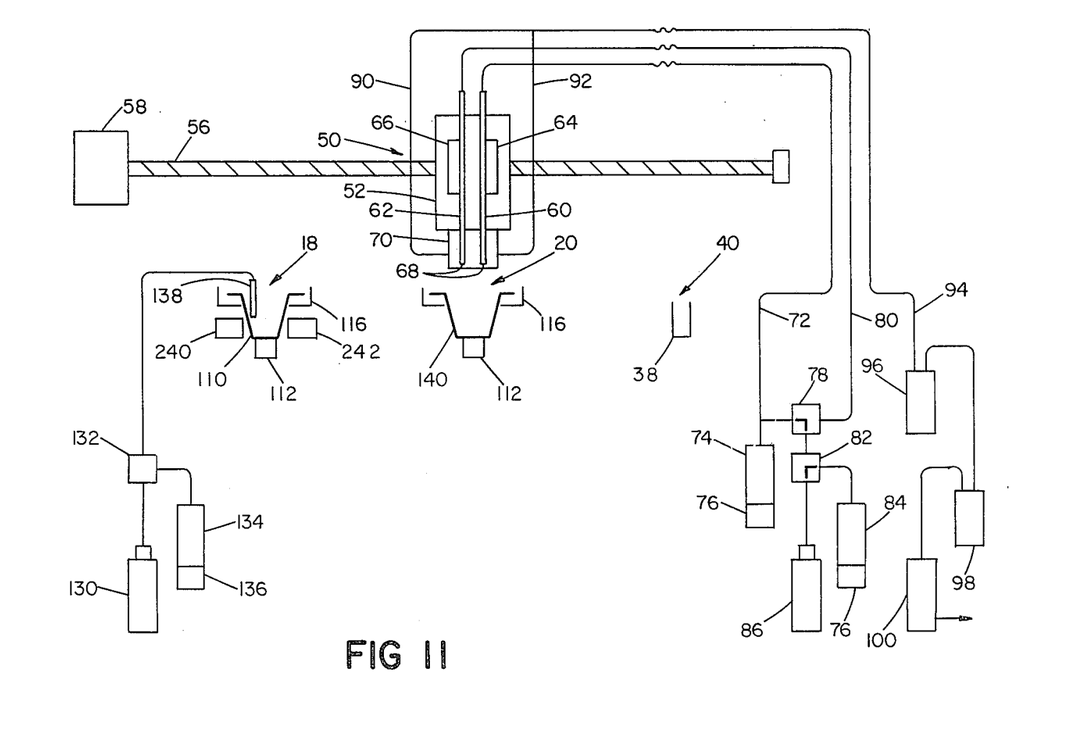

After the several analysis cuvettes 110 have been serviced by probe assembly 50, probe carriage 52 is returned to the utility cup position 20 as indicated in FIG. 11. During that return travel, valve 82 is switched to connect metering device 84 to diluent reservoir 86 and the chamber of metering device 84 is refilled with diluent from reservoir 86. At utility station 20, both probes 60, 62 are lowered into utility cup 140 and the contents of the probes and their storage tubes 72, 80 are discharged into the utility cup with an excess of about two milliliters of diluent. The probes 60, 62 are then returned to their raised position and the utility cup 140 is driven at high speed to discharge the mixture to waste in a flushing and cleaning operation. Probe carriage 52 is indexed back to sample station 40 for withdrawal of the next sample which has been indexed into position by the sample transport mechanism 36. As carriage 52 is returning to the sample station 40, the metering chamber of metering device 74 is refilled with diluent as are storage tubes 72 and 80 and their probes 60, 62.

In the clinical analysis system shown in FIG. 1, the diluent for the chemistry analysis section 12 is a saline solution and the diluent for the electrolyte analysis section 24 is 40 mmol/1 magnesium sulfate (of 160 millimolar ionic strength) buffered to a pH of 8. In an operating sequence of the chemistry analysis section 12 of that system, 100 microliters of sample is withdrawn from sample cup 38 by probe 60C and metering pump 84C. Carriage 52C is then indexed to creatinine analysis station 22 where fifty microliters of sample is dispensed into analysis cuvette 110 at that station by metering pump 84 through probe 60; and its reagent dispenser 134 dispenses 800 microliters of reagent into the analysis cuvette 110 so that the analysis at station 22 is performed at a dilution ratio of seventeen with a total liquid volume of 850 microliters.

After dispensing fifty microliters of sample at station 22, carriage 52C is indexed to utility station 20 and thirty microliters of sample are dispensed from storage tube 72 through probe 60 by high precision metering pump 74, and concurrently 870 microliters of diluent are dispensed from storage tube 80 through probe 62 by metering pump 84. After the sample and diluent are mixed by bidirectional rotation of utility cup 140, probe 62 is reinserted into the utility cup and 565 microliters of diluted sample are withdrawn for storage in storage tube 80 by metering pump 84.

Carriage 52C is then indexed by drive 58C sequentially to BUN analysis station 18 where 75 microliters of diluted sample are dispensed, to glucose analysis station 16 where 175 microliters of diluted sample are dispensed, and to total protein analysis station 14 where 175 microliters of diluted sample are dispensed. After the dispensing of diluted sample at stations 14, 16, and 18 has been completed, transport carriage 52C is returned to utility station 20 for flushing as described above in connection with FIG. 11.

At each analysis station 14, 16, 18, and 22, 800 microliters of the corresponding reagent is dispensed into each analysis cuvette 110 by its dedicated metering pump 134. Thus, at the creatinine analysis station 22, analysis is performed with a fifty microliter sample volume at a test dilution ratio of seventeen; at the BUN analysis station 18, analaysis is performed with a 1½ microliter sample volume at a test dilution ratio of 350; and at the glucose and total protein analysis stations 16 and 14 respectively, analysis is performed with a 5.8 microliter sample volume at a test dilution ratio of 167.

Probe assembly 50E performs a similar sample dilution and distribution sequence in the electrolyte analysis section 24. With transport carriage 52E over sample station 40, 150 microliters of sample is withdrawn from the sample cup 38 through probe 60E for storage in tube 72E. Carriage 52E is then indexed to total CO₂ analysis station 26 where fifty microliters of sample is discharged into mixing cup 140 by precision pump 74 and 350 microliters of diluent is discharged into cup 140 through probe 62 by metering pump 84. Probe carriage 52E is then indexed by motor 58E to analysis station 30 where 30 microliters of sample are dispensed from probe 60E and 1020 microliters of diluent are dispensed from probe 62E to provide a total volume of 1050 microliters and a dilution ratio of 35 at station 30. After mixing, 120 microliters of diluted sample is withdrawn from cup 140 by probe 62E and metering pump 84E. Carriage 52E is then indexed to chloride analysis station 28 wherein 36 microliters of the diluted sample is dispensed into analysis cuvette 110. Concurrently, the dedicated reagent pump 134 at station 28 is dispensing 800 microliters of reagent into analysis cuvette 110 to provide 836 microliters of a diluted sample—reagent mixture, the analysis being performed with the sample volume of about one microliter at a dilution ratio of 835.

With reference again to total $CO_2$ analysis station 26, after the dispensed quantities of sample and diluent are mixed, a positive displacement metering pump draws about 200 microliters of reagent from line 144 through valve 146 into reaction chamber 148, followed by about 210 microliters of a diluted sample from cup 140. Valve 146 is then rotated to a "degassing" position and, as described in copending application Ser. No. 161,375 entitled ANALYTICAL SYSTEM filed June 20, 1980 and assigned to the same assignee as this application, which disclosure is incorporated herein by reference, the volume of reaction chamber 148 is increased to release carbon dioxide. After the "degassing" interval, the volume of reaction chamber 148 is reduced and the pressure of the released gas is measured by transducer 150.

With reference to station 30, after withdrawal of 120 microliters of diluted sample as described above, positive displacement pump 160 is operated to flow about 800 microliters of the diluted sample from cup 140 via probe 140 past the potassium sensing electrode 32, the sodium sensing electrode 34 and reference electrode 156 for analysis. Further details of this analysis station may be had with reference to copending application Ser. No. 175,053 entitled ANALYSIS SYSTEM filed Aug. 4, 1980, and assigned to the same assignee as this application, which disclosure is incorporated herein by reference. After equilabration and measurement, the sample is discharged to waste.

Finally, as carriage 52E is indexed back towards sample station 40, the carriage pauses at station 26 and about 1500 microliters of diluent are dispensed through the probes into cup 140 at station 26 for cleaning and flushing.

The cycle duration for each probe assembly 50C, 50E, as described above, is about one-half minute. Biological fluids such as serum, urine, and CSF, as appropriate, may be analyzed with the system. The system provides rapid handling of small volumes of sample liquids with concurrent analyses being performed with a wide range of dilution ratios.

While a particular embodiment of the invention has been shown and described, various modifications thereof will be apparent to those skilled in the art, and therefore it is not intended that the invention be limited to the disclosed embodiment or details thereof and departures may be made therefrom within the spirit and scope of the invention.

What is claimed is:

1. Analysis apparatus comprising first and second storage chambers, each said storage chamber having a port through which liquid may be flowed into and from said storage chamber, said storage chambers and their ports being arranged to permit concurrent flowing of liquids from both said storage chambers into a processing chamber,
   first and second liquid metering means, a diluent reservoir, and a valve arrangement for connecting one of said metering means to said diluent reservoir and to either of said storage chambers, each said metering means, when connected to a storage chamber, controlling flow of liquid into and out of said storage chamber through its port.

2. The apparatus of claim 1 wherein each said storage chamber is in the form of an elongated flexible tube and each chamber port is formed in a probe member that is connected to said tube.

3. The apparatus of claim 2 wherein each said probe member is mounted for movement into and out of a processing chamber.

4. The apparatus of claim 2 and further including a transport carriage on which two probes are mounted, said transport carriage being arranged for movement between a sampling station where a sample of fluid to be analyzed is drawn into a storage chamber through its associated probe port and a series of analysis stations.

5. The apparatus of any preceding claim wherein each metering means is a positive displacement pump.

6. The apparatus of claim 5 wherein each said positive displacement pump includes a precision bore cylinder under the control of a stepping motor and precision lead screw.

7. The apparatus of any preceding claim wherein one of said metering means has a large capacity than the other metering means.

8. The apparatus of claim 7 wherein the capacity of one metering means is at least ten times the capacity of said other metering means.

9. The apparatus of any one of claims 2-4 and further including a vacuum chamber in which the tips of said probes are housed for extracting liquid from said prove tips.

10. An analysis system comprising
    an analysis station having an analysis cuvette,
    a sample station and a sample container support mechanism for positioning a sample container at said sample station,
    a support with a liquid handling probe mounted thereon,
    a drive for providing relative movement between said probe support and said sample and analysis stations,
    structure mounted in said probe support for housing the end of said probe and having a port, and means to flow air inwardly through said port into said probe housing structure and along an outer surface of said probe for flowing liquid from the tip of said probe over the outer surface of said probe.

11. The system of claim 10 wherein said probe is a hollow tube, said probe housing structure is a cylindrical passage, said port is an open end of said passage, and said probe being mounted on said probe support for movement between a retracted position in which the end of said probe is housed in said passage and a transfer position in which the end of said probe outside of said passage for injecting liquid into or withdrawing liquid from a container aligned with said probe.

12. The system of claim 11 wherein said air flow means includes means to apply reduced pressure to said passage and the clearance between said prove tube and said passage is less than 0.1 millimeter.

13. An analysis system comprising
a plurality of analysis stations, each having an analysis cuvette chamber,
a sample station and a sample container transport mechanism for positioning a sample container at said sample station, a supplementary station having a mixing chamber,
a probe transport carriage with two liquid handling probes mounted thereon,
a drive for moving said transport carriage between said sample station, said analysis station and said supplementary station,
a diluent reservoir,
a main metering pump,
each said liquid handling probe having a storage chamber connected thereto,
a valve arrangement for connecting said main metering pump alternately to said diluent reservoir and to said storage chambers for flowing diluent from said reservoir and for flowing liquid into and out of either of said storage chambers, and
a second metering pump of greater precision than said main metering pump connected to one of said storage chambers for controlling the flow of liquid into and out of the storage chamber connected with said one probe.

14. The system of claim 13 wherein each said metering pump is a positive displacement device that includes a precision bore cylinder with a coaxial reciprocable piston.

15. The system of claim 14 wherein each said piston is driven by a stepping motor through a precision lead screw.

16. The system of claim 15 wherein the cylinder of said second pump has a smaller diameter bore than the cylinder of said main pump.

17. The system of either claim 13 or 16 wherein each said probe is a metal tube, and further including structure mounted on said carriage that defines two parallel passages in which the tips of said probe tubes are housed, a vacuum system connected to said passage for provided flow of air upwardly through each said passage over the lower outer surface of the probe, and wherein said prove is movable between a retracted position in which the probe tip is housed in its passage and a transfer position in which the probe tip is inserted into a chamber at one of said stations for injecting or withdrawing liquid through said probe.

18. The system of anyone of claims 1, 13, or 16 wherein said valve arrangement includes a first three-way valve arranged to alternately connect said two storage chambers to a second three-way valve, the common port of said second three-way valve being connected to said main metering pump with its third port connected to said diluent reservoir.

19. The system of either claim 13 or 16 wherein said analysis station includes a reaction chamber cup mounted for bidirectional rotation and a dedicated reagent dispenser, and said supplementary station also includes a cup mounted for bidirectional rotation into which said two probes may be concurrently inserted.

20. The system of either claim 10 or 13 wherein said drive includes a digitally controlled stepper motor.

21. The system of either claim 13 or 16 wherein each said storage chamber is in the form of an elongated flexible tube, and each said probe is a metal tube resiliently mounted for reciprocating movement between a retracted position and a transfer position in which the end of the probe is inserted into a processing chamber at one of said stations for injecting or withdrawing liquid through said probe.

* * * * *

UNITED STATES PATENT AND TRADEMARK OFFICE
CERTIFICATE OF CORRECTION

PATENT NO. : 4,323,537
DATED : April 6, 1982
INVENTOR(S) : Dinesh I. Mody

It is certified that error appears in the above-identified patent and that said Letters Patent are hereby corrected as shown below:

Column 3, line 22, "pum" should be --pump--.

Column 5, line 19, "spring 194" should be --spring 196--.

Column 8, line 54, "1 1/2" should be --2 1/2--.

Column 9, line 36, "probe 140" should be --probe 142--.

Column 10, line 31, "large" should be --larger--.

Column 10, line 38, "prove" should be --probe--.

Column 10, line 67, "prove" should be --probe--.

Column 12, line 8, "prove" should be --probe--.

Signed and Sealed this

Twenty-ninth Day of June 1982

[SEAL]

Attest:

Attesting Officer

GERALD J. MOSSINGHOFF

Commissioner of Patents and Trademarks